United States Patent [19]

Safford

[11] 4,020,672
[45] May 3, 1977

[54] MECHANICAL FORCE PULSE GENERATOR FOR USE IN STRUCTURAL ANALYSIS

[75] Inventor: Frederick B. Safford, Palos Verdes Estates, Calif.

[73] Assignee: Agbabian Associates, El Segundo, Calif.

[22] Filed: Oct. 9, 1973

[21] Appl. No.: 404,136

[52] U.S. Cl. .................................................. 73/12
[51] Int. Cl.² ........................................ G01N 3/30
[58] Field of Search .............. 73/12, 90; 188/1 C

[56] References Cited

UNITED STATES PATENTS

| | | | |
|---|---|---|---|
| 2,811,385 | 10/1957 | Butler | 188/1 |
| 2,837,176 | 6/1958 | Dropkin | 188/1 |
| 3,100,982 | 8/1963 | Cutler | 73/12 |
| 3,108,503 | 10/1963 | Murek | 73/12 X |
| 3,158,048 | 11/1964 | Bollar | 73/12 X |
| 3,535,912 | 10/1970 | Muller | 73/12 |

Primary Examiner—Herbert Goldstein
Attorney, Agent, or Firm—Edward A. Sokolski

[57] ABSTRACT

A mandrel member has a series of projections formed therein in a predetermined pattern to represent a force-time history to be used in testing a member. A cutter member is provided for shearing off these projections. A driving force is provided so as to cause relative movement between the cutter member and the mandrel to effect the shearing of the projections. Vibratory energy in accordance with the characteristic foce-time pattern of the projection configuration is generated with the shearing action and is transferred to the member to be tested.

17 Claims, 8 Drawing Figures

MECHANICAL FORCE PULSE GENERATOR FOR USE IN STRUCTURAL ANALYSIS

This invention relates to force pulse generators for use in structural analysis, and more particularly to such a generator which mechanically generates a force output by virtue of the cutting action of a cutter member on projections arranged in a predetermined pattern.

It is oftentimes necessary to evaluate the structural capabilities of a piece of equipment or a structural unit to assure that it will function properly in an intended environment or under particular conditions which may arise. Thus, in the case of military equipment which must operate under heavy vibration, or structures which must be capable of withstanding explosive blasts or earthquakes, tests simulating such conditions are made on the equipment or structure in question.

Shock tests are made in several ways. One of these involves the application of an impact shock to the device under test by dropping a weight on the equipment, or dropping the equipment onto a base from a predetermined height, or driving the equipment on a carriage to cause it to impact against a stop. This type of test has the limitation of applying only a single shock characteristic to the device, and thus only simulates a very limited force pattern environment. To simulate a great variety of vibration patterns for application to the device to be tested, electromechanical or electrohydraulic force generators are generally used. With these types of devices, it is possible to electrically or hydraulically generate patterns having any desired force-time history, the electrical or hydraulic energy being amplified and by means of a transducer converted to a force pattern which can be applied to the device under test. While such electromechanical or electrohydraulic force generators are capable of simulating any desired pulsating force pattern, they have the following limitations: First, the amount of output force and displacement that can be generated with an electromechanical or electrohydraulic device are limited by the inherent practical design constraints imposed by the electrical components and hydraulic flow. Further, where the generation of high forces is involved, such electromechanical and electrohydraulic devices are relatively expensive and require high power inputs. Also, electrical equipment and hydraulic equipment present certain maintenance and installation problems which are not encountered in fully mechanical implementations.

This invention provides means for generating a force test signal simulating any given force-time history, which has distinct advantages over prior art electromechanical devices. Firstly, in view of the fact that the present invention generates a force pattern mechanically, it is inherently capable of outputs having higher force and displacement than that of prior art electromechanical or electrohydraulic devices. Further, it is simpler and more economical in its construction and operation than such devices. Also, the device of the invention, in view of its lack of dependency on electrical circuitry or hydraulic valving, tends towards higher reliability and has less requirement for maintenance and repair. It is also to be noted that the device of the invention, in view of its mechanical implementation, avoids the inherent inefficiency involved in transducing energy from electric or hydraulic to mechanical form, as in the aforementioned devices of the prior art.

It is therefore an object of this invention to provide improved means for generating a force pulse output for use in testing equipment and structures.

It is another object of this invention to provide a device capable of generating a pulse output having a precise force-time pattern of higher force and displacement.

It is still another object of this invention to provide a precise force pulse generator capable of generating complex force patterns which is of simpler and more economical construction.

Other objects of this invention will become apparent as the description proceeds in connection with the accompanying drawings, of which:

Briefly described, the device of the invention comprises a mandrel member having projections formed thereon in a predetermined configuration representing a particular force-time pattern to be generated. A cutter member is provided for engaging and shearing these projections. The mandrel and cutter members are driven together with sufficient force by driving either the mandrel, the cutter, or both, so that the projections are in a single stroke sheared off by the cutter member tool. As a result of the shearing action, vibrational energy is generated in members to which the mandrel and cutter members are attached, the vibrational pattern of this energy corresponding to the configuration of the mandrel projections. This vibrational energy is transferred to a member under test.

It has been verified experimentally that if a cutter member is caused to shear off a plurality of serially arranged projections on a mandrel in a single stroke, that a force pattern is generated which is in accordance with the depth, width and length of the projections and the characteristics of the mandrel material. Further, the force-time pattern of the force pulses generated is a function of the relative velocity between the cutting member and the projections, as well as the shape of the projections and their spacing along the longitudinal dimension of the mandrel. Utilizing these parameters, it is possible to analytically determine the parameters of the mandrel projections as well as the operating parameters for obtaining any desired force pattern with the device of the invention. Such analysis can be most conveniently made with the help of a computer, followed by empirical measurements to confirm and refine the initially computed parameters.

Figure 1:
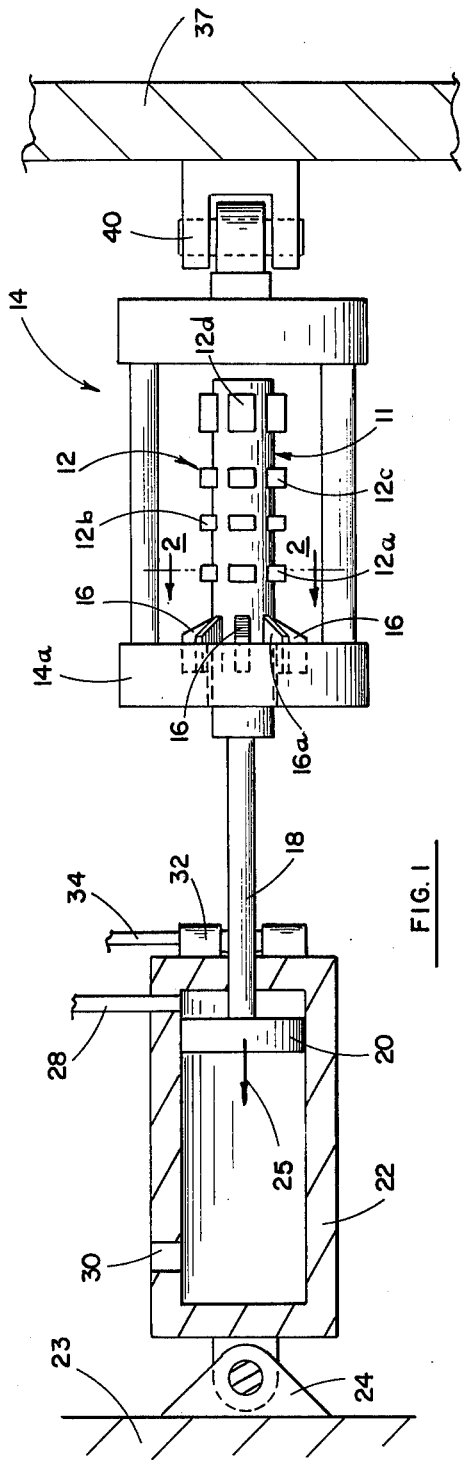
FIG. 1 is an elevational view partially in section of one embodiment of the invention.
Figure 2:
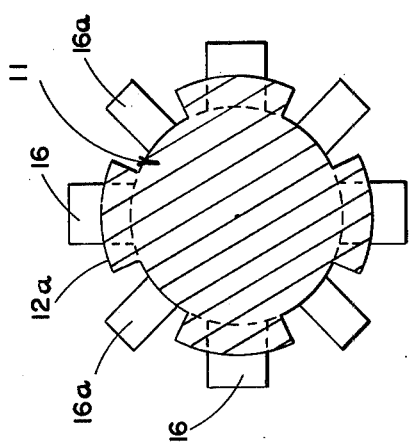
FIG. 2 is a cross sectional view taken along the plane indicated by 2—2 in FIG. 1.

Referring now to FIGS. 1 and 2, a first embodiment of the invention is illustrated. Mandrel 11 may be fabricated of a hard metal, such as steel, or a softer metal such as aluminum or magnesium, depending upon the force pattern requirements. Plastic materials may also be used, such as nylon, polyester, etc. The mandrel which may be generally cylindrical has a plurality of projections 12 formed thereon. These projections are formed in sets 12a–12d, the projections of each set being similar in configuration and arranged in a circle around the circumference of the mandrel. The mandrel projection sets are spaced from each other by distances which are in accordance with the desired force-time pattern to be generated. Further, the dimensions of the projections of each set are determined, as already explained, to provide the desired force pattern. Mandrel 11 is mounted within support frame 14 for slidable motion along the longitudinal axis thereof.

Cutter blades 16 are fixedly mounted in end piece 14a of frame 14, there being a cutter blade for each of the serially arranged projections in each set thereof. Additional passive blades 16a (in the case of the mandrel shown) may be provided for use with mandrels having different configurations. It is to be noted that in the illustrative example, blades 16 have a lesser width than the projections so that they will cut grooves therein rather than removing the projections entirely, this to provide a particular force pattern. As to be pointed out in connection with FIGS. 3 and 4, other dimensional relationships between the cutter blades and the projections can be utilized for obtaining different force patterns.

Mandrel 11 is attached to the drive rod 18 of piston 20. Piston 20 is slidably mounted in cylinder 22 which is anchored on support member 23 by means of shackle 24. Piston 20 may be pneumatically driven in the direction indicated by arrow 25 by a pneumatic drive signal fed to input line 28. Venting for the cylinder is provided by vent 30. The motion of piston 20 can be conveniently controlled by means of pneumatic brake 32 which is mounted to arrest the movement of piston 18 in response to a pneumatic actuation signal fed to line 34. Frame 14 is coupled to a load 37 (i.e., the device under test) to which the force signals are to be transmitted by means of shackle 40.

Thus, when brake 312 is released, piston 18 drives the mandrel with sufficient velocity so as to cause cutter members 16 in a single stroke to cut grooves in all of the serially positioned sets of projections 12a–12d. This cutting action causes a series of force pulses to be generated in frame 14, these pulses being transferred through shackle 40 to load 37. The nature of the force pulses, as already noted, is a function of the dimensions of the projections and the cutters as well as the material of which these elements are fabricated. The force-time pattern of the signals is a function of the velocity at which the mandrel is driven and the shape and longitudinal spacing of the projections.

Figure 3:
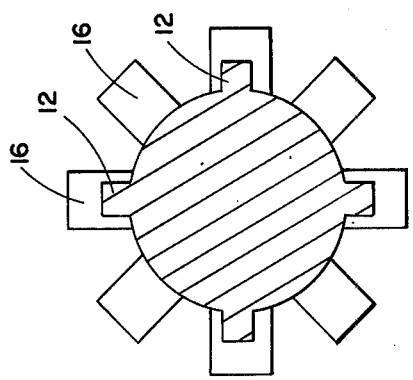
FIG. 3 illustrates an alternative configuration for the cutters and projections which may be used in the device of the invention.

Referring now to FIG. 3, another configuration which may be utilized for cutters 16 as related to projections 12 is illustrated. In this instance, the cutters 16 are wider than the projections 12 so that they totally shear the projections off rather than merely forming grooves therein as in the previous embodiment. This arrangement, of course, will give a different type of force pattern than that for the embodiment previously described.

Figure 4:
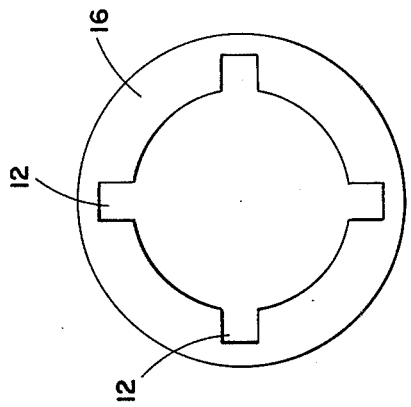
FIG. 4 illustrates another configuration for the cutter and projections which may be used in the device of the invention.

Referring now to FIG. 4, still a further configuration for the cutter 16 is shown. In this instance cutter 16 is in the form of a single conical blade which shears off all of the projections in their entirely. This produces still a different type of force pattern than either of the previously described embodiments.

The cutter-projection combinations illustrated in FIGS. 2–4 are of course only illustrative of several combinations of configurations that can be utilized, and it should be apparent that a great many other combinations of cutter blade and mandrel projection configurations can be employed to provide a great variety of different force pattern characteristics. Other power sources may also be used.

Figure 5:
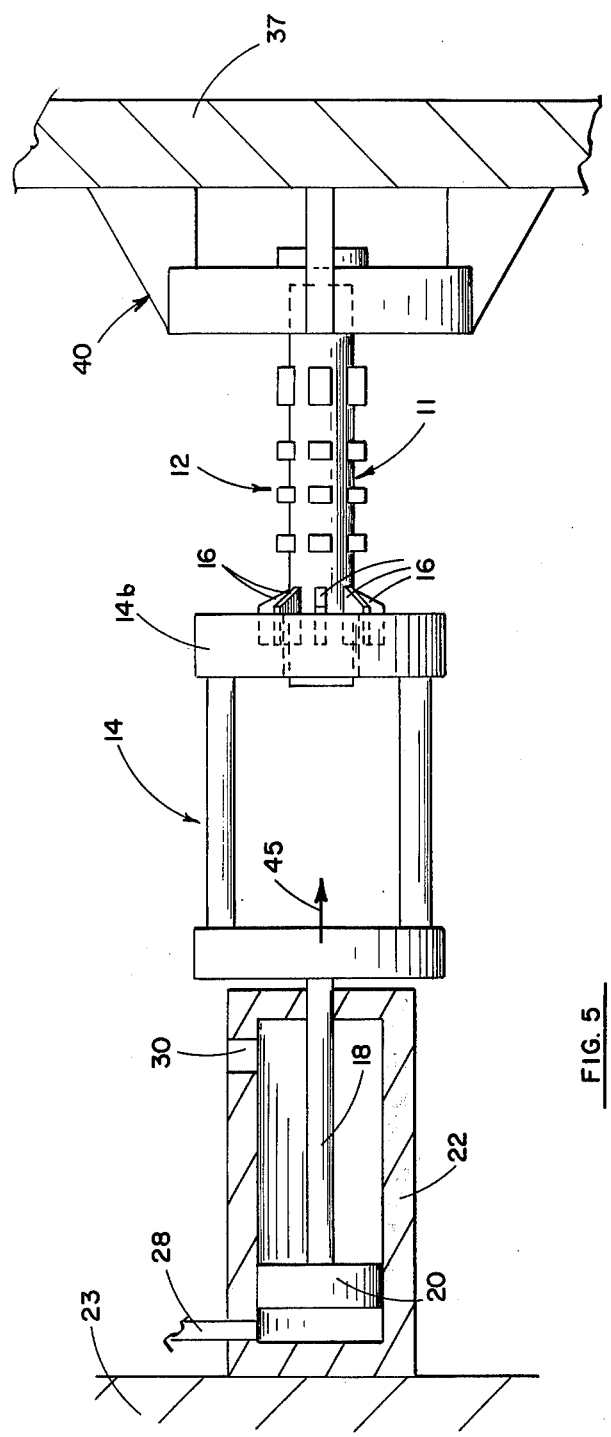
FIG. 5 is an elevational view partially in section of another embodiment of the invention.

Referring now to FIG. 5, another embodiment of the device of the invention is illustrated. This embodiment differs from that of FIG. 1 in that the mandrel 12 is kept stationary and the cutter blades 16 are driven against the projections of the mandrel to effect the shearing action. Mandrel 11 which may be of the same design as that for the embodiment of FIG. 1, is fixedly coupled to load 37 by means of support and attachment member 40. One end of mandrel 11 is slidably supported in the end portion 14b of support frame 14. Cutter blades 16 are fixedly mounted in end portion 14b. Frame member 14 is attached to the rod 18 of piston 20 with cylinder 22 being fixedly supported on support member 23. Piston 20 is driven by a pneumatic drive fed to line 28. When piston 20 is driven in the direction indicated by arrow 45, support frame 14 is driven therewith causing blades 16 to cut through projections 12, thus providing the desired force output through member 40 to the equipment or structure under test.

Figure 6:
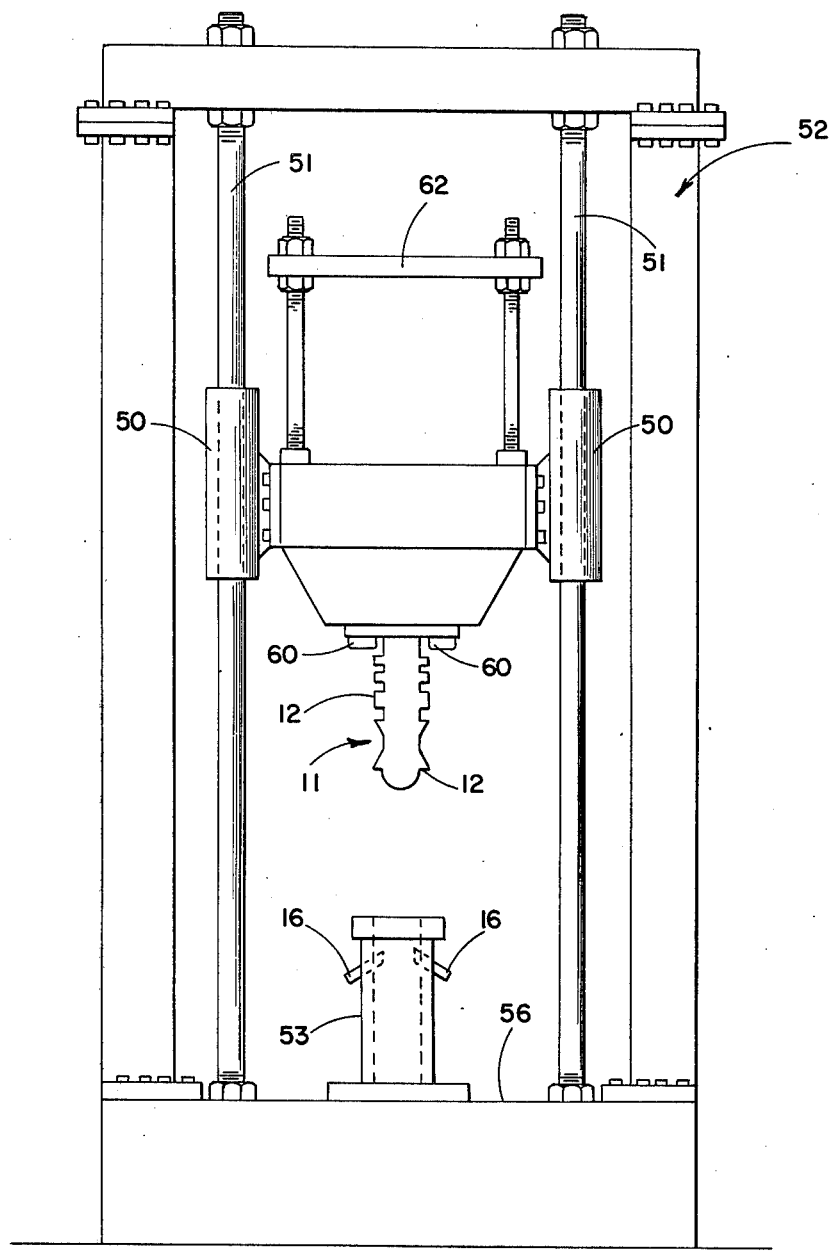
FIG. 6 is an elevational view illustrating a further embodiment of the invention.

Referring now to FIG. 6, still another embodiment of the invention is illustrated, this embodiment being incorporated into a drop shock test machine. Drop carriage 50 is slidably mounted on guides 51, these guides being supported on support frame 52. Attached to the bottom portion of drop carriage 50 is mandrel 11, having projections 12 formed thereon in a predetermined desired configuration. Cutter blades 16 are supported on a tool holder 53 which is supported on the base portion 56 of the support frame. A snubber 60 of resilient material is placed above the mandrel on the bottom of the carriage to arrest the movement of the carriage when the cutting action has been completed.

In the operation of the device, the carriage is released, the mandrel thus being gravity impelled against the cutter blades 16 to provide the desired cutting action of the projections 12. Movement of the carriage is arrested with contact of snubber 60 against the top portion 53a of tool holder 53. The structure to be tested 62 may be supported on the drop carriage, or if so desired, may be coupled to tool holder 53.

Figure 7:
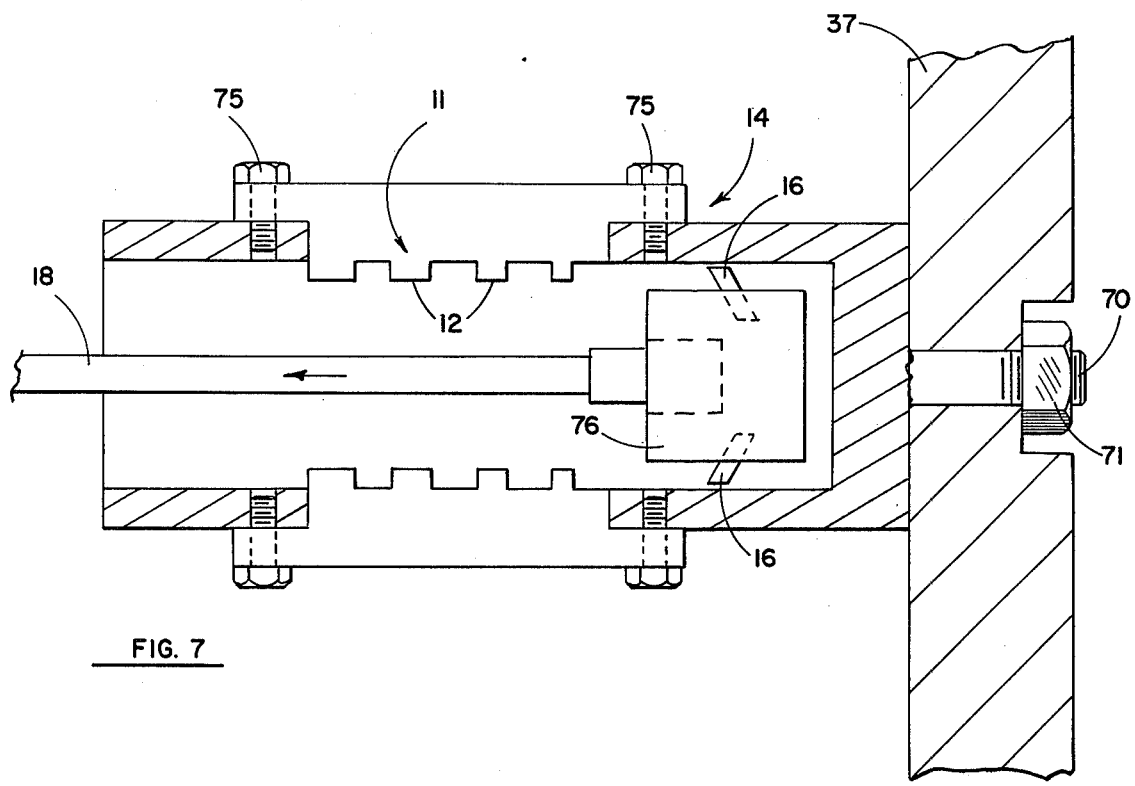
FIG. 7 is an elevational view in section of still another embodiment of the invention.

Referring now to FIG. 7, a further embodiment of the invention is illustrated. This embodiment is generally similar to that of FIG. 1 except for the fact that the mandrel in this instance surrounds the cutter blades, i.e., is external thereto. As shown in the Figure, support frame 14 is attached to load 37 by means of threaded stud 70 and nut 71. Mandrell 11 is attached to frame 14 by means of bolts 75, the mandrel having projections 12 corresponding to the vibration pattern to be generated. Slidably supported in housing 14 is plate member 76 which has a pair of cutter blades 16 extending therefrom. Plate member 76 is connected to a hydraulic piston, such as that described in connection with FIG. 1, by means of drive rod 18. Plate member 76 is driven by means of the piston to cause projections 12 to be sheared off by cutter blades 16 and thus to generate the desired vibration pattern in the same general manner as described for the previous embodiments.

Figure 8:
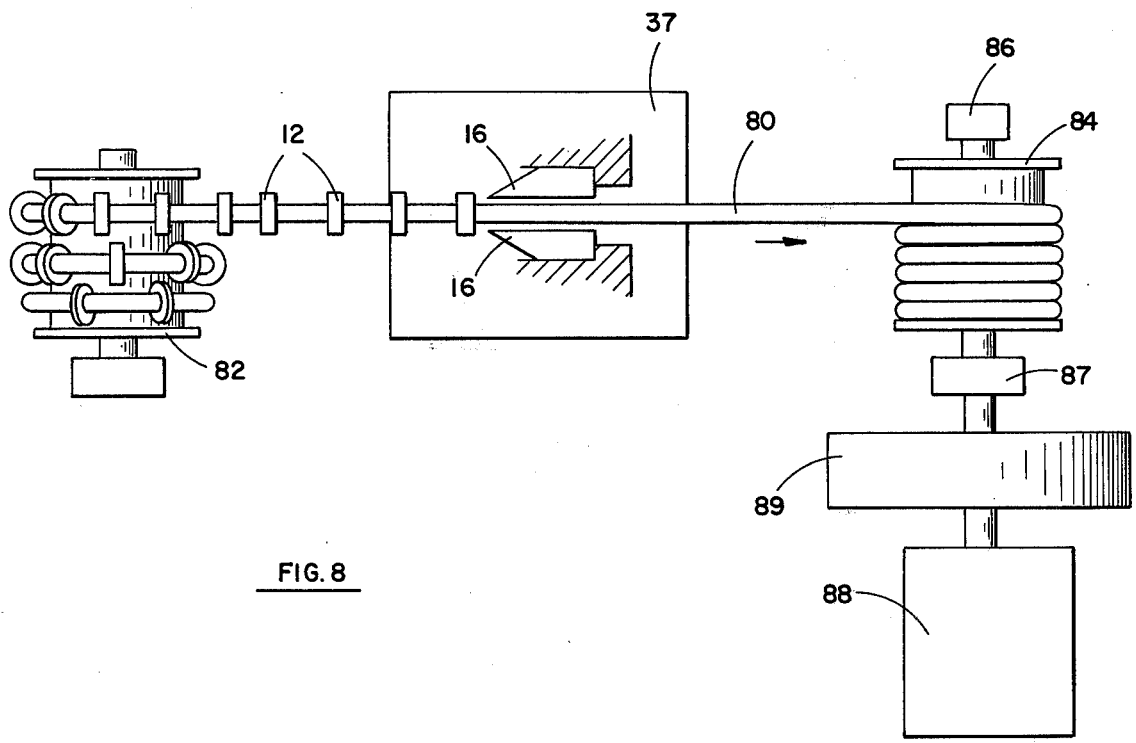
FIG. 8 is an elevational view of a further embodiment of the invention.

Referring now to FIG. 8, still a further embodiment of the invention is illustrated. This embodiment is particularly suitable for generating long time duration force inputs, such as in simulating earthquake shock waves. The mandrel member is formed by cable 80 which may also be a sprocket chain which has a plurality of disc-like projections 12 extending outwardly therefrom along a substantial length thereof. The cable is wound around supply reel 82 and drive reel 84. A brake 86 and clutch 87 are provided for the drive reel to enable the control thereof. Drive reel 84 is rotatably driven by means of motor 88. A flywheel 89 is preferably attached to the drive reel shaft to increase the inertia thereof. Cutter blades 16 are fixedly attached to output load 37.

In the operation of the device, drive reel 84 is brought up to speed before the projections 12 reach the cutter blades such that the projections are driven with high force against the blades to cause the shearing of these projections and thus to effect the desired vibration of the load. This embodiment thus enables the generation of a long time duration force output.

It should immediately be apparent that the device of the invention can be implemented for incorporation into other types of existing shock test machines to equal advantage, using the same basic principles as described herein.

The invention thus provides a simple yet highly effective means for generating force patterns of any desired configuration for use in the testing and evaluation of equipment and structures. In view of the fact that the force patterns are generated mechanically, very high outputs can be achieved as compared with electromechanical and electrohydraulic devices of the prior art.

While the invention has been described and illustrated in detail, it is to be clearly understood that this is intended by way of illustration and example only and is not to be taken by way of limitation, the spirit and scope of this invention being limited only by the terms of the following claims.

I claim:

1. In a device for generating a force having a predetermined force-time pattern in a load member comprising:
    a mandrel having a series of separate and distinct projections formed thereon, said projections being dimensioned, shaped and spaced from each other on said mandrel so as to represent said force-time pattern,
    a cutter member for engaging said projections in succession,
    drive means for causing said cutter member to shear off at least a portion of said projections in succession in a single stroke, thereby generating said force in said mandrel and said cutting member, and means for coupling said force to said load member.

2. The device of claim 1 wherein said cutter member is narrower in width than said projections so that it cuts grooves in said projections.

3. The device of claim 1 wherein said cutter member is at least as wide as said projections whereby said projections are entirely sheared off.

4. The device of claim 1 wherein said cutter member is mounted in a stationary position, said drive means driving the projections of said mandrel against said cutter member.

5. The device of claim 4 wherein said drive means comprises a cylinder having a piston slidably mounted therein, said piston being coupled to said mandrel, and means for driving said piston.

6. The device of claim 4 wherein said drive means comprises a drop carriage and means for slidably supporting said carriage for a gravity drop, said mandrel being mounted on said carriage.

7. The device of claim 4 wherein said mandrel comprises an elongated cable, said drive means comprising a drive reel around which said cable is wound and motor means for rotatably driving said drive reel to wind said cable means therearound.

8. The device of claim 1 wherein said mandrel is mounted in a stationary position, said drive means driving said cutter member against the projections of the mandrel.

9. The device of claim 8 wherein said drive means comprises a cylinder having a piston slidably mounted therein, said piston being coupled to said cutter member, and means for driving said piston.

10. A device for providing a force having a predetermined force-time pattern to a structure to be tested comprising:
    a mandrel having a plurality of separate and distinct projections formed thereon, said projections being dimensioned, shaped and spaced from each other so as to represent said force-time pattern and being positioned serially along said mandrel,
    a cutter member for shearing said projections in succession,
    drive means for causing said cutter member to successively shear off at least a portion of each of the serially positioned projections, thereby generating said force in said mandrel and cutter member, and
    means for coupling said force to said structure to be tested.

11. The device of claim 10 wherein said cutter member comprises a single conical blade.

12. The device of claim 10 wherein said cutter member comprises a plurality of blades spaced from each other around a circle, said mandrel being generally cylindrical and having a plurality of sets of projections, the projections of each set thereof being arranged in a circle at a different point along the longitudinal dimension of said cylinder, the projections of each set thereof each being positioned opposite a separate one of said blades.

13. The device of claim 12 wherein said drive means comprises means for driving said cutter member along the longitudinal axis of said mandrel so as to shear off at least a portion of the projections of each set thereof in succession.

14. The device of claim 12 wherein said drive means comprises means for driving said mandrel along the longitudinal axis thereof against said blades so as to shear off at least a portion of the projections of each set thereof in succession.

15. A method for generating a force signal having multiple pulses forming a predetermined force-time pattern to test a structure comprising the steps of:
    providing a mandrel with a series of projections spaced from each other and having a predetermined pattern representing said force pattern,
    causing said projections to be sheared in succession by a cutter member thereby generating said multiple pulse force signal, and
    coupling said multiple pulse force signal to said structure.

16. The method of claim 15 wherein said cutter member is driven against said projections to shear at least a portion of said projections in a single stroke.

17. The method of claim 15 wherein said mandrel is driven so as to cause said projections to abut against said cutter member to effect the shearing of at least a portion of each of said projections in a single stroke.

* * * * *